United States Patent [19]

Heitmann et al.

[11] Patent Number: 4,558,586
[45] Date of Patent: Dec. 17, 1985

[54] APPARATUS FOR STABILIZING THE PRESSURE OF GASEOUS TESTING FLUID FOR CIGARETTES AND THE LIKE

[75] Inventors: Uwe Heitmann; Heidi Müller, both of Hamburg, Fed. Rep. of Germany

[73] Assignee: Hauni-Werke Körber & Co. KG., Hamburg, Fed. Rep. of Germany

[21] Appl. No.: 565,275

[22] Filed: Dec. 27, 1983

[30] Foreign Application Priority Data

Jan. 11, 1983 [DE]  Fed. Rep. of Germany ....... 3300598

[51] Int. Cl.⁴ .......................................... G01N 15/08
[52] U.S. Cl. .......................................... 73/38; 73/41
[58] Field of Search ................ 73/38, 37, 41, 45, 45.1, 73/45.2; 137/505.25, 505.26

[56]  References Cited

U.S. PATENT DOCUMENTS 3,412,856 11/1968 Esenwein .
3,426,582  2/1969 McArthur et al. ................... 73/45.1
3,543,564 12/1970 Heitmann et al. ........................ 73/41
3,555,883  1/1971 Heitmann ................................ 73/41
4,090,826  5/1978 Hinzmann .
4,121,595 10/1978 Heitmann et al. .
4,154,090  5/1979 Heitmann et al. ........................ 73/38
4,247,754  1/1981 Baier .
4,281,670  8/1981 Heitmann et al. .
4,282,889  8/1981 Dahlgrün .

FOREIGN PATENT DOCUMENTS 2234094  1/1974 Fed. Rep. of Germany .
2922677 12/1980 Fed. Rep. of Germany .

Primary Examiner—Stewart J. Levy
Assistant Examiner—Joseph W. Roskos
Attorney, Agent, or Firm—Peter K. Kontler

[57]  ABSTRACT

Apparatus for stabilizing the pressure of air which is admitted into a cigarette testing device has a relatively large cylindrical vessel one end wall of which has an inlet receiving compressed air from a source by way of several pressure reducing valves and a flow restrictor. The inlet has a large number of openings and is surrounded by a first outlet which is also formed with a large number of openings and allows the major part of admitted air to escape from the vessel. The other end wall of the vessel has a single opening for admission of testing fluid into the testing device. The cross-sectional area of the passage which is defined by the flow restrictor for the flow of air into the vessel is a small fraction of the combined cross-sectional area of openings which form the first outlet, and the combined cross-sectional area of the openings which form the first outlet is a large multiple of the cross-sectional area of the second outlet. The vessel is filled with a diffusor material, such as a series of sieves, a mass of foamed plastic material and/or a mass of fibers. The quantity of air which can be stored in the vessel greatly excess the quantity of air which is required by the testing device for the testing of a cigarette.

15 Claims, 1 Drawing Figure

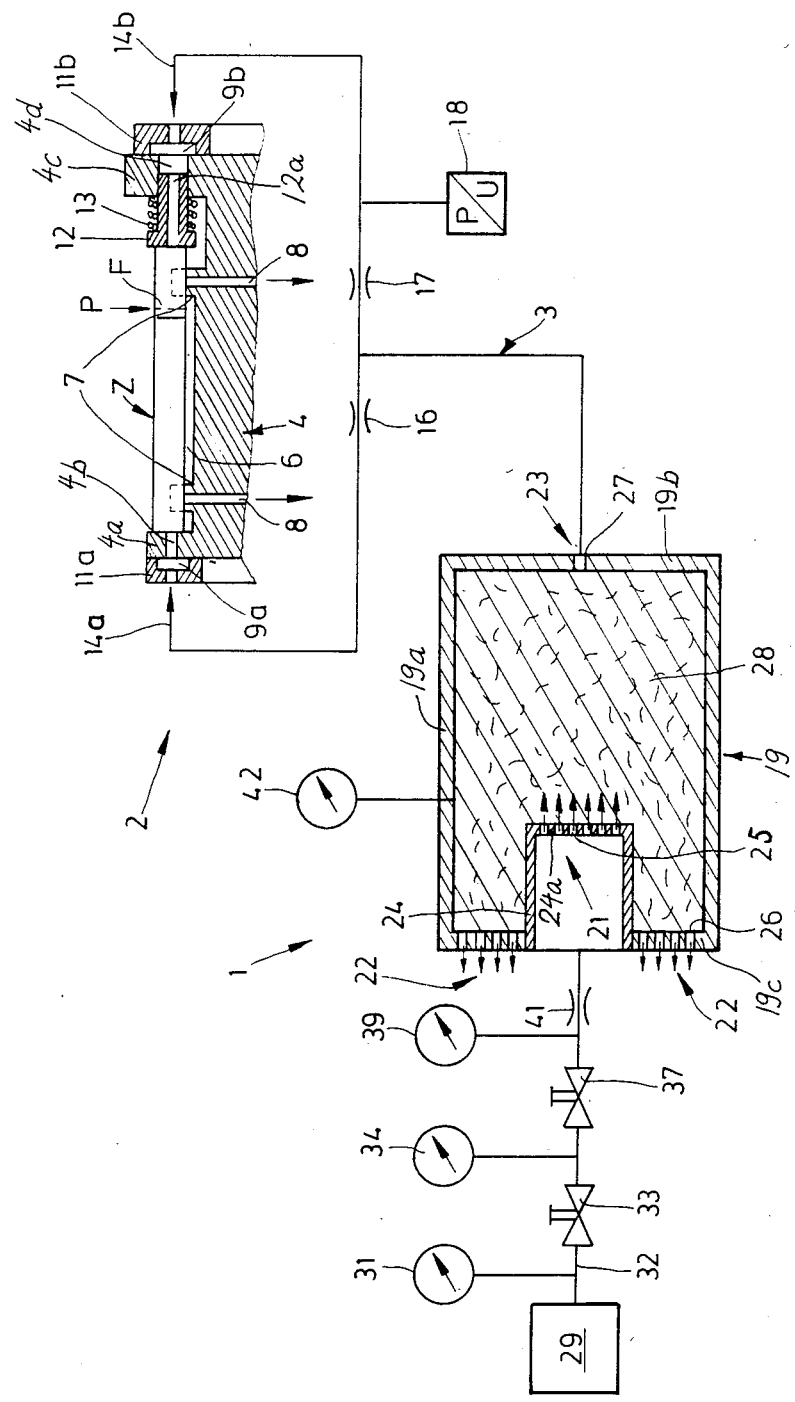

APPARATUS FOR STABILIZING THE PRESSURE OF GASEOUS TESTING FLUID FOR CIGARETTES AND THE LIKE

BACKGROUND OF THE INVENTION

The present invention relates to apparatus for testing plain or filter-tipped cigarettes, cigars, cigarillos, filter rod sections and analogous rod-shaped articles of the tobacco processing industry. More particularly, the invention relates to improvements in pneumatic testing apparatus for such rod-shaped articles. Still more particularly, the invention relates to improvements in apparatus for influencing the gaseous testing fluid which is supplied to pneumatic testing devices for cigarettes or the like.

It is already known to install a pressure regulating system in the conduit which supplies gaseous testing fluid from a suitable source to the testing device for cigarettes or like rod-shaped articles of the tobacco processing industry. It is further known to install in the conduit a vessel whose volume is such that it can store a substantial quantity of testing fluid, namely, a quantity which is a multiple of the quantity of testing fluid that is required for the testing of a single rod-shaped article. The vessel has an inlet which receives testing fluid from the pressure regulating system and an outlet which admits testing fluid to the testing device.

The requirements concerning the accuracy of conditioning the testing fluid prior to admission of conditioned fluid into the testing device depend on the desired degree of accuracy of the testing operation. Thus, the pressure of testing fluid must be stabilized with a very high degree of accuracy if the testing device is to test the rod-shaped articles with a view to ascertain small or minute deviations of the characteristics of such articles from an optimum value. This is the case when the testing device is to monitor the permeability of intentionally perforated portions of the wrappers of plain or filter cigarettes. The purpose of such perforated portions is to admit predetermined quantities of cool atmospheric air into the column of tobacco smoke. Cool atmospheric air is believed to exert a desirable influence upon the percentage of nicotine and condensate in tobacco smoke. The making of perforations involves burning holes into the wrappers (e.g., by resorting to a laser or by causing the web of cigarette paper or other wrapping material to advance through the gaps between a series of electrodes) or the making of holes with resort to needles or the like. Reference may be had to commonly owned U.S. Pat. No. 4,121,595 granted Oct. 24, 1978 to Uwe Heitmann et al. and to commonly owned U.S. Pat. No. 4,281,670 granted Aug. 4, 1981 to Uwe Heitmann et al. for apparatus which perforate a web of wrapping material with one or more laser beams, to commonly owned U.S. Pat. No. 4,247,754 granted Jan. 27, 1981 to Anton Baier for apparatus which perforates a web of wrapping material by sparks during travel of the web between several electrodes, and to commonly owned U.S. Pat. No. 4,090,826 granted May 23, 1978 to Alfred Hinzmann for apparatus which serves to make perforations by mechanical means.

As the sensitivity of the testing device increases, it is necessary to supply to such device a stream of testing fluid whose pressure fluctuates very little or not at all. The perforations in the wrappers of cigarettes or the like are very small so that their detection necessitates resort to highly sensitive testing devices. Presently known testing devices which are used for such purposes react very unfavorably to any, even minor, fluctuations of the pressure of testing fluid which is delivered thereto for the purpose of testing each of a series of successive rod-shaped articles. Any fluctuations of the pressure of admitted testing fluid distort the results of measurements and are likely to lead to ejection of satisfactory articles and/or to retention of unsatisfactory articles.

U.S. Pat. No. 3,426,582 discloses a pressure stabilizing apparatus of the above outlined character which is designed to prevent fluctuations of the pressure of testing fluid from affecting the operation of the testing device proper. German Offenlegungsschrift No. 2,234,094 discloses an apparatus which provides an outlet serving to allow for regulation of the pressure of testing fluid which is admitted to the testing device. A drawback of the just discussed prior apparatus is that they cannot compensate for those fluctuations of the pressure of testing fluid which are attributable to the testing device, especially fluctuations which are attributable to occasional absence of rod-shaped articles at the testing station due to ejection of defective articles ahead of the testing station or which are attributable to the testing of highly defective articles with open seams, large holes, etc. In the absence of a cigarette at the testing station while the testing device discharges testing fluid in anticipation of the presence of an article at the testing station, the testing device discharages a substantial amount of testing fluid which can affect the pressure of fluid that is held in a state of readiness for the next testing operation. Therefore, the testing of the next-following article is not likely to be satisfactory or, if satisfactory for the detection of pronounced defects (such as fully open seams or large holes), is not sufficiently accurate to detect deviations of permeability of the aforediscussed intentionally produced perforations from an optimum permeability.

OBJECTS AND SUMMARY OF THE INVENTION

An object of the invention is to provide a novel and improved apparatus which can stabilize the pressure of testing fluid entering a testing device for cigarettes or the like irrespective of whether the causes for eventual deviations of pressure from an optimum value can be found at the source of testing fluid or in the testing device.

Another object of the invention is to provide an apparatus which can stabilize the pressure of testing fluid with a degree of accuracy exceeding that which is achievable with heretofore known apparatus.

A further object of the invention is to provide an apparatus which can stabilize the pressure of testing fluid entering the testing device irrespective of the frequency at which the device tests the articles and irrespective of the number of defective articles, the absence of articles and/or the extent of defectiveness of certain articles.

An additional object of the invention is to provide the apparatus with novel and improved means for storing a supply of testing fluid upstream of the testing device.

Still another object of the invention is to provide a novel and improved method of preparing testing fluid for admission into a device for the testing of plain or filter cigarettes or other rod-shaped articles of the tobacco processing industry.

A further object of the invention is to provide a cigarette making or processing machine which embodies the above outlined stabilizing apparatus.

An additional object of the invention is to provide novel and improved means for regulating the pressure of testing fluid on its way from the source to the testing device.

A further object of the invention is to provide a novel and improved combination of the above outlined apparatus with a testing device for plain or filter tipped cigarettes, cigars, cigarillos, filter rod sections or analogous rod-shaped articles of the tobacco processing industry.

The invention is embodied in an apparatus for stabilizing the pressure of a gaseous testing fluid (preferably air) which is supplied to a testing device for rod-shaped articles (cigarettes, cigarillos, cigars and/or filter rod sections) of the tobacco processing industry wherein each testing operation involves the consumption of a first quantity of testing fluid (such first quantity can fluctuate within a certain range, depending on the condition and/or the presence or absence of the article which is being or is to be tested). The apparatus comprises a vessel dimensioned to store a second quantity of testing fluid which is a large or very large multiple of the first quantity. The vessel has an inlet for testing fluid, a first outlet for testing fluid and a second outlet whose cross-sectional area is a multiple of the cross-sectional area of the first outlet. The apparatus further comprises first conduit means connecting the first outlet with the testing device, a source of testing fluid (e.g., an air compressor), and second conduit means connecting the source with the inlet of the vessel. Such second conduit means preferably contains suitable pressure regulating means preferably including a flow restrictor whose effective cross-sectional area for the passage of testing fluid from the source to the inlet of the vessel is a fraction (e.g., a very small fraction) of the cross-sectional area of the second outlet. The pressure regulating means can further comprise one or more pressure reducing valves which are installed in series upstream of the flow restrictor.

The inlet can comprise a plurality of openings for admission of testing fluid into the vessel, and the same preferably applies for the second outlet. The first outlet can have a single opening which admits testing fluid into the first conduit means. In accordance with a presently preferred embodiment of the invention, the vessel comprises a tubular (e.g., cylindrical) wall, a first end wall which closes one end of the tubular wall and is provided with the first outlet, and a second end wall which closes the other end of the tubular wall and is provided with the inlet as well as with the second outlet, e.g., in such a way that the openings of the second outlet form an annulus surrounding the openings of the inlet.

The apparatus preferably further comprises diffusor means for testing fluid. Such diffusor means is installed in the vessel between the inlet and the two outlets and can include a body of foamed synthetic plastic material with open cells so that the testing fluid can be caused to flow from the inlet to each of the two outlets.

The cross-sectional area of each opening of the second outlet can equal or approximate the cross-sectional area of each opening of the inlet. The inlet can be placed nearer to the second outlet than to the first outlet.

The novel features which are considered as characteristic of the invention are set forth in particular in the appended claims. The improved pressure stabilizing apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

The single FIGURE of the drawing is a diagrammatic partly elevational and partly sectional view of a pressure stabilizing apparatus which embodies one form of the invention and is connected to a testing device for filter cigarettes.

DESCRIPTION OF THE PREFERRED EMBODIMENTS

The drawing shows a pressure stabilizing apparatus 1 which embodies the present invention and serves to supply testing fluid to a testing device 2 for filter cigarettes Z. The pressure stabilizing apparatus 1 comprises an elongated cylindrical vessel 19 having an outlet 23 comprising a single opening 27 serving to admit testing fluid to a conduit 3 which, in turn, supplies the testing fluid to the testing device 2. The testing device 2 comprises a rotary drum-shaped conveyor 4 serving to transport a succession of equidistant parallel filter cigarettes F toward, through and beyond a testing station between the slots 9a, 9b of two stationary valve plates 11a, 11b which are adjacent to the respective end faces of the conveyor 4. The periphery of the conveyor 4 is formed with axially parallel flutes 6 serving as a means for receiving filter cigarettes Z and having pairs of ribs 7 traversed by radially extending suction ports 8 which attract the filter cigarettes Z to the respective ribs 7 so that the tobacco-containing end of each cigarette is adjacent to the valve plate 11a and the filter plug F of each cigarette Z is adjacent to the valve plate 11b. The suction ports 8 are connectable to a suction generating device (not shown) by way of a suitable stationary valve plate in a manner not forming part of the present invention. It suffices to say that the cigarettes Z are held in the respective flutes 6 during travel from a first transfer station where they are transferred onto the conveyor 4 and a second transfer station where they enter the flutes of a further conveyor, not shown. The conveyor 4 has a flange 4a which is adjacent to the valve plate 11a and has an annulus of axially parallel bores 4b, one for each of the flutes 6. A second flange 4c of the conveyor 4 has an annulus of bores 4d for reception of the shanks of axially movable sealing elements 12 which are biased by springs 13 to engage the end faces of the respective filter plugs F and which can be retracted by a suitable cam to allow for introduction of successive cigarettes Z into the respective flutes 6 as well as for removal of tested cigarettes from such flutes. The bore 12a of each sealing element 12 registers with one of the bores 4b in the flange 4a. For example, the testing device 2 can be constructed, assembled and operated in a manner as disclosed in commonly owned U.S. Pat. No. 3,543,564 granted Dec. 1, 1970 to Bob Heitmann et al., in commonly owned U.S. Pat. No. 3,555,883 granted Jan. 19, 1971 to Uwe Heitmann or in commonly owned U.S. Pat. No. 4,154,090 granted May 15, 1979 to Uwe Heitmann et al. The conduit 3 has two branches 14a, 14b which respectively deliver testing fluid to the slots 9a, 9b so that the testing fluid can enter both ends of that cigarette Z which passes through the testing station. The branches 14a, 14b of the conduit 3 respectively contain preferably adjustable flow restrictors 16, 17. The purpose of the flow restrictor 17 is to ensure that the testing device 2 is most sensitive in the region of the filter plug F of that cigarette Z which is located at the testing station. This is desirable because the wrappers of the filter plugs F are normally provided with perforations P serving to admit cool atmospheric air into the column of tobacco smoke when the cigarette is lighted and the smoker draws smoke into his or her mouth. The branch 14b communicates with an electropneumatic transducer 18 downstream of the flow restrictor 17. The transducer 18 serves to generate signals which are indicative of the condition of tested cigarettes; such signals are utilized to segregate defective cigarettes Z from satisfactory cigarettes, either on the conveyor 4 or on one of the next-following conveyors. A transducer which can be used in the testing device 2 is disclosed, for example, in commonly owned U.S. Pat. No. 3,412,856 granted Nov. 26, 1968 to Albert Esenwein. This patent discloses a diaphragm transducer whose diaphragm assumes any one of a number of different positions as a function of the pressure of testing fluid in the respective portion of the branch 14b and wherein the position of the diaphragm is monitored by a suitable capacitor. The manner in which the signals which are transmitted by the transducer 18 can be processed in a cigarette rod making or filter tipping machine is disclosed, for example, in commonly owned U.S. Pat. No. 4,282,889 granted Aug. 11, 1981 to Rolf Dahlgrün.

The vessel 19 of the stabilizing apparatus 1 comprises a tubular (preferably cylindrical) wall 19a one end portion of which is sealed by a first end wall 19b containing the aforementioned opening 27 of the first outlet 23, and the other end portion of which is closed by a second end wall 19c. The central portion 24 of the end wall 19c is cupped and its bottom wall 24a contains a substantial number of openings 25 in the form of bores preferably having identical diameters and together constituting an inlet 21 of the vessel 19. The non-recessed portion of the end wall 19c has an annulus of openings 26 which together constitute a second outlet 22 of the vessel 19. The bottom wall 24a of the cupped portion 24 of the end wall 19c resembles a finely perforated nozzle of the type used in showers, and the same applies for the non-recessed annular portion of the end wall 19c. The openings 25 of the inlet 21 distribute the testing fluid which is admitted into the recessed or cupped portion 24 by a second conduit 32 connecting the inlet 21 with the outlet of an air compressor 29 or another suitable source of testing fluid. The combined cross-sectional area of openings 26, which constitute the outlet 22, is a large multiple of the cross-sectional area of the single opening 27 of the outlet 23. Also, the diameters of openings 26 are preferably identical with the diameters of the openings 25.

In a pressure stabilizing apparatus which was actually tested and put to use in combination with a cigarette testing device, the outlet 22 was formed by a total of fifty openings 26 in the form of bores each having a diameter of 1.4 mm. The diameter of the single opening 27 of the outlet 23 was the same. The inlet 21 consisted of openings 25 in the form of bores each having a diameter of approximately 1.4 mm, and the number of such holes was identical to that of the number of holes 26. However, it is equally possible to replace the inlet 21 with a different inlet, e.g., in the form of an air permeable wall which consists of a suitable porous material. The number of openings 25 forming the inlet 21 can exceed or can be less than the number of openings 26. The volume of the vessel 19 is such that it can store a substantial quantity of testing fluid, namely, a large multiple of the quantity of testing fluid which is used up to complete a single testing operation, which is used up as a result of the absence of a cigarette Z at the testing station between the slots 9a and 9b at a time when the presence of a cigarette is anticipated, or which is used up when a strongly defective cigarette is located between the aforementioned slots (e.g., a cigarette whose tobacco-containing portion has an open seam so that a relatively large quantity of testing fluid can escape into the surrounding atmosphere). As a rule, the quantity of testing unit which is used up for the testing of a single cigarette is very small because a satisfactory cigarette will permit the escape of very small quantities of testing fluid through the perforations P and perhaps of some testing fluid through the permeable wrapper of the tobacco-containing portion of the cigarette Z between the slots 9a, 9b. For example, the volume of the vessel 19 can be 2 cubic decimeters or thereabout.

The pressure stabilizing apparatus 1 preferably further comprises a diffusor 28 which fills the interior of the vessel 19 and may constitute a body or mass of fibrous material or a body or mass of foamed synthetic plastic material with open cells. Such material further enhances the diffusing action of numerous openings 25 which constitute the inlet 21.

The conduit 32 is connected with a first pressure gauge 31 immediately downstream of the source 29, with a second pressure gauge 34 downstream of a first pressure reducing valve 33, and with a third pressure gauge 39 downstream of a second pressure reducing valve 37 which is in series with the valve 33. For example, the pressure in that portion of the conduit 32 which is connected to the pressure gauge 31 may be in the range of 5 bar. The valve 33 reduces such pressure to 2 bar, and the valve 37 further reduces the pressure to 5000 mm water column. Such relatively high pressure is further reduced by a preferably adjustable flow restrictor 41 which is installed in the conduit 32 between the gauge 39 and the inlet 21 of the vessel 19. The cross-sectional area of the passage which is defined by the flow restrictor 41 for the flow of testing fluid from the valve 37 toward the inlet 21 is a small fraction of the combined cross-sectional area of openings 26 which form the outlet 22. For example, the flow restrictor 41 can reduce the pressure of testing fluid from 5000 to 50 mm water column. The pressure in the interior of the vessel 19 is indicated by a further gauge 42.

The major percentage of the relatively large quantity of testing fluid which enters the vessel 19 by way of the numerous openings 25 of the inlet 21 is permitted to escape via openings 26 of the outlet 22. The diffusing and damping effect of the diffusor 28 upon the testing fluid which flows into the opening 27 of the outlet 23 is so pronounced that the pressure of fluid leaving the vessel 19 at 27 is not subject to any uncontrolled dynamically induced fluctuations. Moreover, even very pronounced fluctuations of pressure in the conduit 3 are compensated for in the interior of the vessel 19 so that they cannot reach the conduit 32 which supplies testing fluid to the inlet 21. This is due to the provision of the diffusor 28 as well as to the relatively large volume of the vessel 19. These features of the improved pressure stabilizing apparatus 1 further ensure that eventual fluctuations of pressure in the conduit 32 downstream of the flow restrictor 41 cannot influence the pressure in the conduit 3, i.e., that the vessel 19 acts as a buffer which effectively prevents the influencing of inflowing testing fluid by the fluctuations at the outlet 23 and/or the influencing of outflowing testing fluid by the fluctuations at the inlet 21. Thus, the apparatus 1 effectively shields the fluid in the conduit 3 from adverse influence of pressure fluctuations in the conduit 32 and vice versa.

An important advantage of the improved pressure stabilizing apparatus is that the effective cross-sectional area of the passage which is defined by the flow restrictor 41 is a small fraction of the combined cross-sectional area of openings 26 which form the outlet 22. This renders it possible to install the flow restrictor 41 downstream of one or more pressure reducing valves (33, 37) which can reduce the pressure from a very high pressure (in the source 29) to a pressure that is still well above the pressure which is best suited for admission of fluid into the vessel 19. The provision of valves 33 and 37 (which can handle large quantities of fluid at elevated pressures) is desirable and advantageous because they ensure that eventual pronounced fluctuations of the pressure of fluid that leaves the source 29 cannot be felt at the inlet 21 of the vessel 19 or are not felt to an extent which could adversely influence the operation of the testing device 2. In other words, the components 33, 37 and 41 of the pressure regulating means in the conduit 32 ensure that the relatively large vessel 19 can properly handle the inflowing testing fluid, especially in conjunction with the diffusor 28, so that the pressure at the outlet 23 is always within an acceptable range.

Another advantageous feature of the improved pressure stabilizing apparatus resides in the provision of an inlet 21 which is formed of a large number of openings 25, i.e., of an inlet which resembles the nozzle in a shower and which can effectively handle the dynamic pressure of testing fluid entering the vessel 19. This is desirable and advantageous because the illustrated inlet 21 prevents the propagation of a single concentrated stream or jet of testing fluid toward and into the opening 27 of the outlet 23. The diffusing action of the inlet 21 is further enhanced or supplemented by the material 28 in the interior of the vessel 19.

As mentioned above, and as shown in the drawing, the outlet 22 preferably also comprises a number of openings 26 not unlike the nozzle in a shower. This reduces the impact of testing fluid upon the non-recessed portion of the end wall 19c and the development of eddy currents in the interior of the vessel 19, especially along the inner sides of the walls 19a, 19b, 19c. The inlet 21 cooperates with the outlet 22 to suppress the so-called "noise" of testing fluid which is attributable to the dynamically induced part of the pressure of testing fluid and which, in the absence of any preventive measures, would adversely influence the evaluation of test signals because the "noise" is superimposed upon the test signals.

The illustrated bottom wall 24a of or the entire recessed portion 24 of the end wall 19c can be replaced with an insert of sintered metal which provides a maze of narrow passages for the flow of testing fluid from the flow restrictor 41 into the interior of the vessel 19. The same applies for that portion of the end wall 19c which is formed with the openings 26. The diffusing action of the material 28 in the interior of the vessel 19 is enhanced due to the fact that the inlet 21 and the outlet 23 are provided in two different end walls (19c, 19b) of the vessel.

The diffusor 28 also contributes to a pronounced reduction of the aforementioned dynamically induced "noise" by suppressing dynamically induced fluctuations of the pressure of testing fluid that flows from the inlet 21 toward the outlet 23. More specifically, the diffusor 28 prevents the development of turbulence in the interior of the vessel 19 and effectively shields the testing fluid, which enters the conduit 3, from undesirable influences of testing fluid that flows beyond the flow restrictor 41 and enters the vessel 19 via inlet 21. A similar diffusor is disclosed (but for a different purpose) in German Offenlegungsschrift No. 2,922,677. This German publication discloses the use of diffusors in pneumatic brakes to reduce the noise level. The aforementioned materials (foams or fibers) can be replaced with a set of sieves or, alternatively, one or more sieves can be used in combination with one or more fibrous or foamed inserts.

It has been found that the improved pressure stabilizing apparatus contributes significantly to reliability of the testing operation in a cigarette rod making, filter tipping or analogous machine for the making and/or further processing of rod-shaped tobacco-containing products. The pressure stabilizing apparatus is effective not only when the testing station of the device 1 (or an analogous testing device) receives rod-shaped articles at regular intervals but also if one or more articles are missing so that the slots 9a and 9b are permitted to discharge testing fluid into the atmosphere whenever they register with a pair of bores 4b, 4d which do not flank a filter cigarette Z. In other words, the apparatus 1 can adequately stabilize the pressure of testing fluid which flows into the conduit 3 under ideal circumstances (when the device 2 tests a series of satisfactory cigarettes Z with minimal escape of testing fluid via perforations P and pores of the wrapping material) as well as when the conditions deviate considerably from optimum conditions, e.g., during testing of a highly defective cigarette or when one or more cigarettes are absent so that the testing fluid is permitted to escape into the atmosphere during the entire interval which is allotted for the testing of a discrete rod-shaped article. This is attributable, to a considerable degree, to the provision of the outlet 22 which permits the escape of a relatively large quantity of testing fluid, namely, a quantity which is a multiple of the quantity required to complete a single testing operation. Due to such dimensioning of the outlet 22, the main flow of testing fluid in the interior of the vessel 19 is from the inlet 21 toward the outlet 22 so that the pressure at the inlet 21 can be much higher than at the outlet 23 with the result that fluctuations of fluid pressure at the outlet 23 are negligible or nil even if the fluctuations of pressure at the inlet are rather pronounced. Such dimensioning of the outlet 22 exhibits the additional advantage that the apparatus 1 can employ a much simpler and less sensitive pressure regulating means. In other words, the pressure regulating means can employ commercially available valves (33, 37) which can handle fluids at elevated pressures and can regulate the flow of large quantities of testing fluid.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. Apparatus for stabilizing the pressure of a gaseous testing fluid which is supplied to a testing device for rod-shaped articles of the tobacco processing industry wherein each testing operation involves the consumption of a first quantity of testing fluid, comprising a vessel arranged to store a second quantity of testing fluid which is a multiple of said first quantity, said vessel having an inlet and first and second outlets and the cross-sectional area of said second outlet being a multiple of the cross-sectional area of said first outlet; first conduit means connecting said first outlet with the testing device; a source of testing fluid; and second conduit means connecting said source with said inlet.

2. The apparatus of claim 1, further comprising pressure regulating means installed in said second conduit means.

3. The apparatus of claim 1, further comprising a flow restrictor installed in said second conduit means and having an effective cross-sectional area for the passage of testing fluid which is a fraction of the cross-sectional area of said second outlet.

4. The apparatus of claim 1, wherein said inlet has a plurality of openings for admission of testing fluid into said vessel.

5. The apparatus of claim 1, wherein said second outlet has a plurality of openings for evacuation of testing fluid from said vessel.

6. The apparatus of claim 1, wherein said vessel has a tubular wall having first and second end portions, a first end wall closing one end portion of said tubular wall and provided with said first outlet, and a second end wall closing the other end portion of said tubular wall and provided with said inlet and said second outlet.

7. The apparatus of claim 1, further comprising diffusor means for testing fluid, said diffusor means being installed in said vessel intermediate said inlet and said outlets.

8. The apparatus of claim 7, wherein said diffusor means includes a body of foamed material having open cells.

9. The apparatus of claim 1, wherein said second outlet surrounds said inlet.

10. The apparatus of claim 1, further comprising pressure regulating means installed in said second conduit means, said pressure regulating means including a plurality of pressure reducing valves which are disposed in series.

11. The apparatus of claim 10, wherein said pressure reducing means further comprises flow restrictor means disposed downstream of said plurality of valves, as considered in the direction of flow of testing fluid from said source to said inlet.

12. The apparatus of claim 1, wherein said first outlet has a single opening and said second outlet has a plurality of openings.

13. The apparatus of claim 12, wherein said inlet has a plurality of openings and the cross-sectional areas of each opening of said second outlet at least approximates the cross-sectional area of each opening of said inlet.

14. The apparatus of claim 1, wherein the testing fluid is air.

15. The apparatus of claim 1, wherein said inlet is nearer to said first outlet than said second outlet.

* * * * *